(12) United States Patent
Caponetti et al.

(10) Patent No.: US 8,252,334 B2
(45) Date of Patent: Aug. 28, 2012

(54) DRY POWDER PHARMACEUTICAL COMPOSITIONS COMPRISING SURFACTANTS, HYDROPHOBIC ACTIVE PRINCIPLES, AND WATER-SOLUBLE EXCIPIENTS, PROCESS OF PREPARING, AND STABLE AQUEOUS SUSPENSIONS THEREOF

(75) Inventors: Giovanni Caponetti, Piacenza (IT); Mariella Artusi, Parma (IT); Loretta Maggi, Piacenza (IT); Paolo Corvi Mora, Piacenza (IT)

(73) Assignee: Eratech S.r.l., Milan (IT)

( * ) Notice: Subject to any disclaimer, the term of this patent is extended or adjusted under 35 U.S.C. 154(b) by 1237 days.

(21) Appl. No.: 11/578,661

(22) PCT Filed: Apr. 21, 2005

(86) PCT No.: PCT/EP2005/004277
§ 371 (c)(1),
(2), (4) Date: Oct. 18, 2006

(87) PCT Pub. No.: WO2005/102283
PCT Pub. Date: Nov. 3, 2005

(65) Prior Publication Data
US 2007/0224276 A1    Sep. 27, 2007

(30) Foreign Application Priority Data
Apr. 23, 2004 (IT) .................. MI04A0795

(51) Int. Cl.
*A61K 9/00* (2006.01)
*A61K 9/10* (2006.01)
*A61K 9/14* (2006.01)

(52) U.S. Cl. .......................... 424/489; 424/46
(58) Field of Classification Search .......... 424/46, 424/489
See application file for complete search history.

(56) References Cited

U.S. PATENT DOCUMENTS

| | | | |
|---|---|---|---|
| 6,001,336 A | 12/1999 | Gordon et al. | |
| 6,187,765 B1 | 2/2001 | Harris et al. | |
| 6,780,508 B1 * | 8/2004 | Caponetti et al. | 428/403 |
| 6,946,117 B1 * | 9/2005 | Schutt et al. | 424/45 |
| 7,524,834 B2 * | 4/2009 | Karlsson et al. | 514/174 |
| 7,541,022 B2 * | 6/2009 | Staniforth et al. | 424/46 |
| 2004/0045546 A1 * | 3/2004 | Hirsh et al. | 128/200.14 |

FOREIGN PATENT DOCUMENTS

| | | |
|---|---|---|
| WO | WO 98/31346 | 7/1998 |
| WO | WO 99/16422 | 4/1999 |

OTHER PUBLICATIONS

Online definition of "between" accessed at mathworld.wolfram.com/between.html on Mar. 23, 2011.*

* cited by examiner

*Primary Examiner* — James H. Alstrum-Acevedo
(74) *Attorney, Agent, or Firm* — Jacobson Holman PLLC (57) ABSTRACT

Pharmaceutical composition in a dry powder form comprising at least one hydrophobic active principle, at least one water-soluble excipient and at least one surfactant, wherein the particles in said dry powder state have a Volume Mean Diameter $VMD_d$ greater than the Volume Mean Diameter $VMD_w$ of particles in a suspension obtained from said pharmaceutical composition at standard conditions of dispersion in a water-medium. It is also disclosed a process to prepare such dry composition and an extemporaneous suspension for inhalation therapy obtainable from said dry composition.

13 Claims, 3 Drawing Sheets

DRY POWDER PHARMACEUTICAL COMPOSITIONS COMPRISING SURFACTANTS, HYDROPHOBIC ACTIVE PRINCIPLES, AND WATER-SOLUBLE EXCIPIENTS, PROCESS OF PREPARING, AND STABLE AQUEOUS SUSPENSIONS THEREOF

This is a nationalization of PCT/EP05/004277 filed Apr. 21, 2005 and published in English.

The present invention relates to a pharmaceutical composition in the form of dry powder, to its preparation process, to a stable aqueous suspension obtained from said pharmaceutical composition and to a kit designed for an extemporaneous preparation of said suspension.

A distinctive aspect of the invention is directed to a pharmaceutical composition in the form of powder, granulate, tablets or similar, capable of generating—through an extemporaneous preparation—a fine suspension of a drug or active principle, or particles containing said drug or active principle, in an aqueous medium. Said fine suspension of the drug is intended, preferably, but not exclusively, for an inhalation therapy.

BACKGROUND OF THE INVENTION

In case of an inhalation therapy, the particles of any drug must be deposited in the deepest pulmonary region, where the most important pharmacological actions occur. For this to happen, said particles must be fine and such as to avoid a premature deposition in the upper respiratory tract. It is indeed known that the respiratory tract operates against aerosolized particles as a filter, along which said particles are captured and deposited according to their size. The particle size range useful for inhalation, to achieve optimal deposition of the drug, usually lies between 0.1 and 10 μM, ideally between 0.5 and 5 μm. It is also reported that particles below 0.1 μm can be exhaled by the patient instead of being deposited in the deepest pulmonary region.

Figure 1:
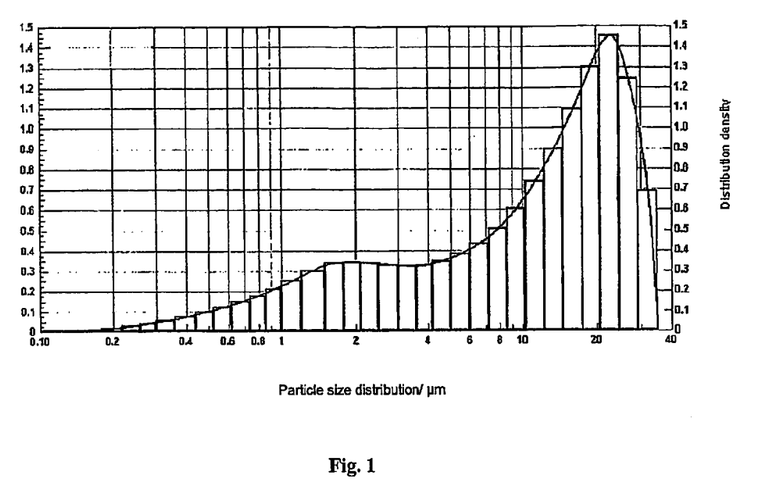

The preparation of fine pharmaceutical suspensions, even if widely common, can present some inherent difficulties that can ultimately affect their physical stability. In particular, the critical aspect influencing the physical stability of a fine suspension is related to the formation at rest of a sediment of drug which, due to the presence of surfactants and proper salts in the medium, should allow for rapid dispersion of the sediment and reconstitution of the original homogeneous suspension. A difficult re-dispersion of this sediment in the suspension, however, can cause the patient to withdraw an incorrect dosage of drug from the container, either exceeding or lacking the correct one. FIG. 1 shows the dimensional distribution of a commercial inhalation suspension, from which it is clear that the particles have a very strong tendency to aggregate, leading to sediments of large size aggregated particles and bi-modal size distributions. In the common practice of fine suspensions preparations, such as inhalation suspensions, the drug in a coarse dry powder state, is previously micronized to reduce its particle size below 5 μm. This dimensional reduction, performed in the dry state, leads to an initial aggregation of the drug particles. In order to break these initial aggregates and to maintain primary drug particles individually separated for the entire life of the product, the preparation of the inhalatory suspension is normally carried out by "wetting" the drug in advance with surfactants, suspending it in an aqueous solution containing salts and using high-energy mixers to mechanically break the aggregations of the drug particles. In such case, the physical stability is theoretically assured by the formation at rest of a weakly flocculated sediment that the patient would re-suspend shaking the container before its use. However, the formation of these weak floccules is not guaranteed, and the majority of inhalation products in suspension show drug sediments made of strongly aggregated particles that cannot be re-dispersed, causing irregularities in the administered dosage.

A further difficulty in the preparation of pharmaceutical suspensions relates to the chemical instability of certain drugs in an aqueous medium, which remarkably limits the shelf-life of the product. In these cases the drug is preferably administered, when possible, in the powder form.

Another problem of pharmaceutical suspensions relates to the control of microbial proliferation in inhalation products in aqueous form. The simplest approach has been, until now, the use of preservatives, which in some cases can lead to allergic reactions in the patient and sometimes do not guarantee the preservation of the product against certain microorganisms. The microbial contamination of a pharmaceutical composition can be better controlled by using a dry, powder form composition.

An example of the complexity of the preparation of inhalation pharmaceutical suspensions—concerning both the process and the required ingredients—is described in the U.S. Pat. No. 6,187,765. Moreover, FIG. 1 shows the size distribution of the particles in a freshly prepared suspension, that appears to be bi-modal, with a first peak around 1.2-1.3 μm and a second peak around 3 μm. The suspension therefore does not consist of homogeneous particles. As previously indicated, it is known that in these types of suspensions the particles have the tendency to aggregate over time and to originate multi-modal size distributions, with proportionally significant fractions of large size aggregates. The result is a reduction of the effective administered drug dosage during the inhalation therapy.

U.S. Pat. No. 6,001,336 describes a method to prepare drugs in powder form for inhalation therapy via spray drying of suspensions of said drugs. Considering that the final goal of the method is the production of fine powders for inhalation, lower than 5 μM in diameter, the method is rather expensive and not so much efficient. For example, the spray drying phase has to be performed in a way to generate about 20 μm drops and the collection and separation of the dry particles can require different treatments and the use of non-conventional equipments. Dry particles are characterized by the absence of surfactant or the presence of a low amount of surfactant compared to that of the drug, with a weight-to-weight surfactant/drug ratio never greater than about 0.5.

An aspect of the invention is therefore to provide a dry powder pharmaceutical composition that can be prepared using a relatively simple method and is able to generate—by an extemporaneous dispersion in an aqueous medium performed in mild conditions—a stable pharmaceutical suspension in which the dispersed drug or active ingredient particles have size such as to optimize the actually administrable dosage.

This and other objects and advantages of the invention, which will appear from the following description, are achieved by a pharmaceutical composition in a dry powder form containing a hydrophobic active principle, one or more water-soluble excipients, and one or more surfactants, characterized by particles with a Volume Mean Diameter ($VMD_d$) greater than the Volume Mean Diameter ($VMD_w$) of particles of a suspension obtained from said pharmaceutical composition in an aqueous medium under standard conditions of dispersion. Another aspect of the invention consists in a preparation process of a dry powder pharmaceutical composition including a hydrophobic active principle, one or more water-soluble excipients and one or more surfactants, wherein the Volume Mean Diameter ($VMD_d$) of the particles of said dry solid composition is greater than the Volume Mean Diameter ($VMD_w$) of the particles of a suspension obtained from said composition in aqueous-medium under standard conditions of dispersion, said process including:

a) preparing a first phase (A) in which said hydrophobic active principle is present in a suitable liquid medium;
b) preparing a second phase (B) in which one or more water-soluble excipients are dissolved in an aqueous medium;
c) dissolving the surfactants in either one of phase (A) or phase (B) above, depending on the surfactant preferential solubility;
d) mixing said phases (A) and (B) to obtain a phase (C) in which the liquid medium is homogeneous;
e) drying said phase (C) in controlled conditions in order to obtain a dry powder with particle size between 0.1 and 175 μm;
f) collecting said dry powder and shaping it in a suitable form for an extemporaneous preparation of a suspension.

Another aspect of the invention refers to a stable aqueous suspension of particles comprising a hydrophobic active principle, obtained by an extemporaneous dispersion of a dry powder pharmaceutical composition in an aqueous medium, comprising a hydrophobic active principle, at least one water-soluble excipient and at least one surfactant, characterized by the fact that the Volume Mean Diameter ($VMD_w$) of the particles in said suspension is lower than the Volume Mean Diameter ($VMD_d$) of the particles of said dry powder composition, wherein said Volume Mean Diameter ($VMD_w$) is determined under standard conditions of dispersion in an aqueous medium.

A further aspect of the invention consists of a kit comprising a predetermined amount of the dry powder composition of the invention and a known volume of an aqueous dispersing medium, such as the contact of said composition and said dispersing medium generates said stable aqueous suspension of said hydrophobic active principle, ready to use.

BRIEF DESCRIPTION OF THE DRAWINGS

FIG. 1 shows the dimensional distribution of a commercial inhalation suspension.

FIG. 2 is a graph showing particle size evaluated by light scattering in humid state conditions plotted against time of complete sedimentation evaluated with the Lumifuge centrifuge.

FIG. 3 shows the dry state (curve A) and wet state (curve B) particle size distribution related to Example 4.

FIG. 4 shows the dry state (curve A) and wet state (curve B) particle size distribution related to Example 6.

FIG. 5 shows the dry state (curve A) and wet state (curve B) particle size distribution related to Example 8.

FIG. 6 shows the dry state (curve A) and wet state (curve B) particle size distribution related to Example 17.

DETAILED DESCRIPTION OF THE INVENTION

The term "standard conditions of dispersion in aqueous medium" means those conditions at which an amount of dry powder composition, variable with respect to its active principle content, is dispersed under stirring for 3 minutes in a Sucell SVA (Small Volume Adapter) dispersion cell of a light scattering Sympatec Oasis analyzer for humid state—analysis, such as to detect, through the light scattering analyzer, an optimal light obscuration. The analysis is conducted generally using a lens for the dimensional range 0.10-35.0 μm or if necessary a lens for the range 0.5-175.0 μm. Data are calculated and expressed on a volume distribution basis.

The dry powder composition according to the invention includes a drug or hydrophobic active principle, one or more water-soluble excipients, one or more surfactants and possibly other ingredients.

According to the invention, the term "drug or hydrophobic active principle" is referred to any substance with a therapeutic or biological activity which is insoluble or slightly soluble in water. More in particular, the term hydrophobic is referred to substances whose water-solubility is below 10 g/l, usually below 1 g/l and in some cases below 0.01 g/l. If possible, such drug or hydrophobic active principle is soluble in organic solvents such as ethanol or other low molecular weight aliphatic alcohols.

The active principle can include two or more substances in the same form, for example one coating the other, or one dispersed in a matrix of the other, or a mixture of two or more active principles. Common examples of such formulations include active drugs coated with excipients or encapsulated into them, or solid dispersions of the active principles with excipients, with the excipient present to modify the release velocity or to actuate the "targeting" of the active principle.

Examples of pharmacological active principles that can be administered by inhalation include: $\beta_2$-agonists; steroids such as glucocorticosteroids (preferably anti-inflammatory drugs); anticholynergic drugs; leukotriene antagonists and agonists, inhibitors of leukotriene synthesis; pain relievers in general such as analgesic and anti-inflammatory drugs (including steroids and non-steroid anti-inflammatory drugs); cardiovascular drugs such as glycosides; respiratory drugs; antiasthma agents; bronchodilators; anticancer agents; alkaloids (e.g. ergot alkaloids) or triptans such as sumatriptan or rizatriptan that can be used against migraine; drugs (e.g. sulphonylurea) used against diabetes and related dysfunctions; hypnotic and sedative drugs; general anesthetics, psychic energizers; appetite inhibitors; anti-arthritis drugs; antimalaria drugs; antiepileptic drugs; antithrombotic drugs; antihypertensive drugs; anti-arrhythmia drugs; antioxidant drugs; anti-depressive drugs; anti-psychotic drugs; anxiolytic drugs; anti-seizure drugs; anti-emetic drugs; anti-infective drugs; anti-histaminic drugs; anti-fungus and anti-viral drugs; drugs against neurological dysfunctions such as anti-Parkinson drugs (dopamine agonists); drugs against alcoholism and other addiction forms; vasodilators used against erectile dysfunction; muscle relaxants; muscle contractors; opioids; stimulant drugs; relaxant drugs; antibiotics such as macrolides; aminoglycosides; quinolones and β-lactam drugs, vaccines; cytokines; growth factors, hormones, including birth-control drugs; sympathomimetic drugs; diuretics; lipid regulator agents; anti-androgen agents, anti-parasitical drugs; blood thinners; neoplastic drugs; anti-neoplastic drugs; hypoglycemia drugs; nutrient and integrator agents; growth integrators; anti-enteric agents; vaccines; anti-bodies, diagnostic and radio-opaque agents; or mixtures of above mentioned substances (e.g., combinations against asthma including steroids and β agonists), anesthetics and general anesthetic drugs.

Said active principles belong to one or more structural classes, including, but not limited to, small molecules (preferably small insoluble molecules), peptides, polypeptides, proteins, polysaccharides, steroids, nucleotides, oligonucleotides, polynucleotides, fats, electrolytes, and similar substances.

Specific examples include $\beta_2$ agonists salbutamol, salmeterol (as salmeterol xinafoate or other form), formoterol (as formoterol fumarate or other forms), fenoterol and isoproterenol, steroids such as beclomethasone (as beclomethasone dipropionate or other forms), budesonide, mometasone (as mometasone furoate or other forms), fluticasone (as fluticasone propionate or other forms), triamcinolone (as triamcinolone acetonide or other forms), prednisone, prednisolone, methylprednisolone, betamethasone, hydrocortisone, dexamethasone and cortisone. With respect to peptides and proteins, the present invention includes the synthetic, recombinant, native, glycosylated and non-glycosylated ones and active biological fragments, and similar substances.

Active principles for which an immediate release in the blood stream in order to have a rapid pharmacological effect is particularly beneficial include the ones used against migraine, nausea, insomnia, allergic reactions (including anaphylactic reactions), neurological and psychiatric disorders (in particular panic attacks and other psychic or nervous disorders), erectile dysfunction, diabetes and related diseases and cardiac diseases, anti-seizures drugs, bronchodilators and pain relievers and anti-inflammatory drugs.

Examples of such substances are steroids and their salts, such as budesonide, testosterone, progesterone, flunisolide, triamcinolone, beclomethasone, betamethasone, dexamethasone, fluticasone, methylprednisolone, prednisone, hydrocortisone and similar; peptides such as cyclosporine and other water-insoluble peptides; retinoids such as cis-retinoic acid, 13-trans-retinoic acid and other vitamin A and β-carotene derivatives; vitamins D, E and K and their water-insoluble precursors and derivatives; prostaglandins, leukotriens and their activators and inhibitors, included prostacyclin, prostaglandins $E_1$ and $E_2$, tetrahydrocannabinol, pulmonary surfactant lipids, hydrophobic antioxidants, hydrophobic antibiotics and chemotherapy drugs such as amphotericin B, adriamycin, and similar substances.

The water solubility of the soluble excipient or excipients of the present invention is greater than 5 g/l and often greater than 100 g/l or more. They are preferably chosen among sugars, salts and amino acids and have the twofold function to minimize the effects of the inhaled composition on the cellular fluids balance, and to stabilize the aqueous suspension obtained from the dry composition. With respect to the composition in its dry powder form, the excipient constitutes also the solid matrix in which the drug or active principle is dispersed. Examples of soluble excipients used in the composition according to the invention are: alitame, acesulfame potassium, aspartame, sodium saccharin, sodium cyclamate, sucralose, trehalose, xylitol, citric acid, tartaric acid, natural or synthetic aminoacids, peptides and proteins, cyclodextrins, dextrins, hydroxyethylcellulose, gelatin, malic acid, maltitol, maltodextrins, maltose, polydextrose, tartaric acid, sodium or potassium bicarbonate, sodium or potassium chloride, phospholipids, lactose, saccharose, glucose, fructose, mannitol, sorbitol.

Among the favorite soluble excipients are alkaline metals salts such as sodium chloride or potassium chloride, and sugars such as lactose.

The surfactant of the pharmaceutical composition according to the invention may be chosen among different classes of pharmaceutical use surfactants.

Among those substances which may be considered usable surfactants of this invention are all those substances characterized by having a medium-to-low molecular weight and containing a hydrophobic portion, which is usually readily soluble in an organic solvent but weakly soluble or completely insoluble in water, and a hydrophilic (or polar) portion, which is weakly soluble or completely insoluble in an organic solvent but readily soluble in water.

Surfactants are classified based on their polar portion. Therefore surfactants with a negatively charged polar portion are called anionic surfactants while cationic surfactants have a positively charged polar portion. Non-charged surfactants are generally called non-ionic surfactants while surfactants with both negatively and positively charged groups are called zwitterions.

Examples of anionic surfactants are the salts of fatty acids (better known as soaps), sulphates, sulphate ethers and phosphate esters. Cationic surfactants are frequently based on polar groups containing amine groups. The most common non-ionic surfactants are based on polar groups containing oligo-(ethylene-oxide) groups. Zwitterions are usually characterized by a polar group consisting of a quaternary amine and a sulphoric or carboxylic group.

Examples of invention surfactants belonging to the class above are: benzalkonium chloride, cetrimide, sodium docusate, glyceryl monooleate, sorbitan esters, sodium lauryl sulphate, polysorbates, phospholipids, biliary salts.

Surfactants belonging to the family of lecithins are widely used in the food, cosmetic and pharmaceutical industry to improve dispersibility and wettability of poorly soluble compounds. The designation "lecithin" is used for natural mixtures of various phospholipids and their accompanying substances. Lecithins are generally derived from Egg or Soybean eventually leading to lecithins with different compositions. Preferred lecithins for the present inventions are those derived from egg and commercially known as Lipoid E PC-3 as they are characterized by approximately 99% of saturated phosphocholines with palmitic acid content of 34% and stearic acid content of 57%. Also synthetic phospholipids or mixtures of phospholipids can be used in the composition of the invention, in particular those belonging to the families of phosphatidyl choline, phopshatidyl glycerol, phosphatidic acid and phosphatidyl ethanolamine.

Non-ionic surfactants such as polysorbates and polyoxyethylene and polyoxypropylene block copolymers, known as "Poloxamers", are preferred. Among the Poloxamer family of surfactants the commercially known "Pluronic F68", a poloxamer with average molecular weight of 8400, is preferred. Polysorbates are described in the CTFA International Cosmetic Ingredient Dictionary as mixtures of sorbitol fatty acids and esters and sorbitol anhydride condensed with ethylene oxide, known as "Span". Particularly preferred are non-ionic surfactants of the series known as "Tween", more particularly the surfactant known as "Tween 80", a polyoxyethylene sorbitan monooleate available on the market.

The pharmaceutical composition according to the invention may include other components, such as pH buffers and preservatives, but said components are usually not necessary because the composition is stored in dry powder state and the related aqueous suspension is prepared extemporaneously before use.

The term "dry powder composition" refers to a powder, granules, tablet or any other solid state composition with such humidity content to assure a chemically stable composition. More in particular, the term "dry" refers to a solid composition containing less than 10% water (w/w), usually less than 5% and if possible less than 3% (w/w).

The amount of surfactant in the dry powder composition of the invention may vary in a wide range. Usually, the surfactant/active principle weigh-to-weight ratio ranges between 0.1 and 100, preferably between 0.3 and 80, more preferably 0.6 and 40.

The particle size in the dry powder composition of the invention ranges between 0.1 and 175 μm, preferably between 0.5 and 30 µm, and more preferably between 1 and 10 µm, expressed as volume mean diameter VMD.

Preferably the size distribution of the particles in the dry powder composition is concentrated around one peak, which means it is substantially mono-modal.

The preparation process of the dry powder composition according to the invention comprises the following steps:
a) preparing a first phase (A) in which said hydrophobic active principle is present in a suitable liquid medium;
b) preparing a second phase (B) in which one or more water-soluble excipients are dissolved in an aqueous medium;
c) dissolving the surfactants in either one of phase (A) or phase (B) above, depending on the surfactant preferential solubility;
d) mixing said phases (A) and (B) to obtain a phase (C) in which the liquid medium is homogeneous;
e) drying said phase (C) in controlled conditions in order to obtain a dry powder with particle size between 0.1 and 175 µm;
f) collecting said dry powder and shaping it in a suitable form for an extemporaneous.

Phase (A) can be a suspension of the hydrophobic active principle in an aqueous or non-aqueous medium or a solution of the hydrophobic active principle in a suitable non-aggressive organic solvent.

The preparation of a solution is preferred, and the organic solvent is chosen among those miscible with water. In this case, also phase (C) is a solution of all components of the desired composition.

When instead phase (A) is a suspension of the hydrophobic active principle in an aqueous medium, phase (C) too is a suspension in an aqueous medium, and will contain the soluble components, such as excipients and surfactants. Step e) consists of removing the solvent or dispersing liquid medium from phase (C), in order to obtain a dry powder with desired particle size. This removal of solvent or dispersing medium is preferably obtained by spray drying. The nozzle features and the operation parameters are chosen in order to evaporate the liquid medium from the solution or suspension (C) and to obtain a powder with desired properties. If possible, said particle size, expressed as VMD, ranges between 0.1 and 175 µm.

Preferably the size distribution of the particles is substantially mono-modal.

The obtained powder is partitioned as it is in tablets or other suitable form. The relatively large particle size of the dry composition according to the invention is particularly beneficial for various reasons. As already indicated, larger particles have a lower tendency to aggregate compared to fine ones. Moreover, the spray drying process yield could be greater than the one achieved with commercially known processes used to manufacture fine dry inhalation powders. Also, the collection and manipulation of such powder is improved.

The above described dry powder pharmaceutical composition is intended for preparing a stable extemporaneous suspension of the hydrophobic drug or active principle in a proper volume of dispersing fluid, preferably water or physiological solution.

As already indicated, an extemporaneous preparation of a suspension is one performed at the time of use, which is right before the administration of the drug to the patient. In the present description, the term "extemporaneous preparation" also includes a preparation done by a pharmacist or other healthcare practitioner and administered to a patient in a relatively short period of time after the preparation. More in general, an extemporaneous preparation is considered a suspension not directly prepared by the pharmaceutical industry and put on the market to be used as it is, but prepared at a time following the preparation of the dry powder composition, usually at a time close to the administration to the patient.

The suspension according to the invention can be administered to a patient in various ways. Though the suspension is particularly suitable for an inhalation administration, it can also be administered in other parenteral (i.e. non-enteral or non-oral) or oral way.

According to an aspect of the present invention, the Volume Mean Diameter ($VMD_w$) of the powder particles in the suspension is lower than the Volume Mean Diameter ($VMD_d$) of the particles in the dry powder composition. It is to be considered that the lower diameter of the particles in suspension is just partially due to the solubilization of the excipients and surfactant in the aqueous medium. It was indeed surprisingly found that the solubilization effect alone is not sufficient to explain this characteristic feature of the invention, since soluble excipients are also present in powder formulations where the $VMD_d$ is greater than the $VMD_w$, as shown in examples that will follow.

Such feature, expressed by the relationship $VMD_w < VMD_d$, shows three benefits: a) to provide an easier manipulation of the dry composition, since it can be prepared with larger particle size than the one required for an optimal administration, to eliminate or reduce the typical problems related to fine powders, b) to provide a stable suspension, c) to optimize the actual administrable drug dosage in an inhalation therapy.

According to another aspect of the invention, extemporaneous suspensions prepared from a dry powder composition according to the invention, are very stable.

It is known from the literature that a suspension is considered stable if rapid phase separations due to sedimentation do not occur when the density of the particle is greater than the one of the dispersing liquid medium. Therefore the suspension stability is referred to the tendency that said suspension shows to act against the formation of large particle aggregates which separate from the medium. Said stability of the suspension was studied to assess the sedimentation tendency using a Lum GmbH Lumifuge centrifuge working at 300 rpm. Said instrument is able to measure the variation of transmittance of an opaque suspension under centrifugation against time. The variation of the transmittance over time was therefore used to evaluate the tendency to sediment of the suspension. The effect of the centrifugation accelerates the sedimentation, allowing for a rapid evaluation of the physical stability of the suspension. The effect of a 300 rpm centrifugation corresponds indeed to a 12-times increase of the gravity acceleration impressed on the sample. Said gravity increase has been considered useful to accelerate sedimentation in pharmaceutical suspensions in such a way that the acceleration impressed on the sample would not alter the physicochemical interactions between the particles and the dispersing medium.

Through the Lumifuge centrifuge, the transmittance of a 2 ml suspension sample in a test tube is measured in several spots of said tube along a definite length of the portion of tube where the liquid is confined by the centrifugation action. Said measurements help drawing the transmittance profile of the sample, which is then integrated in order to calculate the % transmittance of the sample. The values of % transmittance, recorded every 10 seconds, are plotted against time. It is therefore possible to draw a transmittance profile, typically a straight line, indicating the variation of the % transmittance over time. The slope of said transmittance profile describes the sedimentation velocity of the tested sample, since the transmittance of a sample is a function of the presence of particles in suspension.

In case of samples that do not reach complete sedimentation (100% transmittance) during the measurement time, the slope is calculated using every available data. The value of sedimentation velocity (K) is used to calculate the time of complete sedimentation (100% of transmittance) of the tested sample through the following equation:

$$T_{100} = \frac{\left(\frac{100}{K}\right)}{6}$$

where:
$T_{100}$=time of complete sedimentation
K=slope of the transmittance line According to another aspect of the invention, the time of complete sedimentation of extemporaneous suspensions according to the invention, calculated with the above described method, is greater than 40 minutes, preferably greater than 60 minutes, more preferably greater than 100 minutes.

Referring to the extemporaneous suspensions prepared according to the invention, it was moreover surprisingly found that the behavior of the particles in suspension is distinctive of particles with a lower diameter compared to the actually measured one and expressed as $VMD_w$. The diameter evaluated based on particles in suspension was called Theoretical Mean Diameter TMD. It is evaluated using the following described method.

Sedimentation of a spherical particle in a liquid medium is essentially driven by the Stokes Equation, here reported in a form that shows sedimentation time:

$$\tau = \frac{9\alpha\eta}{2gr^2(\rho_s - \rho_l)}$$

where:
$\tau$=sedimentation time (minutes)
$\alpha$=sedimentation deepness (mm)
$\eta$=dynamic viscosity of the medium (mPas)
g=acceleration gravity (9.81 m/s$^2$)
r=solid particles radius
$\rho_s$=solid particle density (g/cm$^3$)
$\rho_l$=liquid medium density (g/cm$^3$)

Such equation is minimally modified in case sedimentation occurs due to centrifugation. In this case, in fact, the gravity force is substituted by $\omega^2$, the square of the angular speed, and $r_0$, the radius of the centrifuge. The equation becomes:

$$\tau = \frac{9\alpha\eta}{2\omega^2 r_0 r^2(\rho_s - \rho_l)}$$

Using the equation above it is possible to compare, through the time of complete sedimentation, different suspensions, by preparing the samples in a way such as to reproduce the same operative conditions in terms of liquid viscosity and centrifugation parameters. In these operative conditions it is possible to compare the behavior of particles of the same material but different size, using the following equation:

$$\tau_{ref} r_{ref}^2 = \tau r^2$$

where:
$\tau_{ref}$=sedimentation time of the reference
$r_{ref}$=mean radius of a reference particle
$\tau$=sedimentation time of the unknown sample
r=mean radius of an unknown particle sample Such equation has been set up to compare the sedimentation time evaluated for suspensions obtained from dry powder compositions according to the invention, against the sedimentation time of suspensions of each active principle, suspended in a solution with the same final composition of the suspension of the invention. Therefore starting from $\tau_{ref}$ (sedimentation time of the standard suspension of each active principle), $r_{ref}$ (mean radius of the standard particles of each active ingredient) and $\tau$ (sedimentation time of the extemporaneous suspensions prepared according to the invention), it is possible to calculate r and from this it is possible to calculate TMD, which is 2r, according to the formula:

$$TMD = 2 \cdot \sqrt{\frac{\tau_{ref} r_{ref}^2}{\tau}}$$

Another aspect of the invention is therefore consisting of the fact that extemporaneous suspensions prepared according to the invention are characterized by a theoretical mean diameter TMD lower than $VMD_w$, that is TMD<$VMD_w$, preferably TMD≦0.5 $VMD_w$.

It is important to underline that some insoluble active principles, when tested for reference sedimentation measurement by dispersing them in the mixture of surfactant and soluble excipient equivalent to the extemporaneous preparation, did not disperse at all in the aqueous medium making impossible to measure their sedimentation time. In this case it is indeed very clear the benefit provided by the invention as it allows for the formation of stable suspensions with these active principles.

The effect of the formation of stable suspensions, though not completely clarified, could be due to a series of occurrences which, during the extemporaneous dispersion of the dry powder in the liquid medium, lead to the dissolution of the soluble excipients and the formation of insoluble drug particles characterized by having greater suspension stability.

Figure 2:
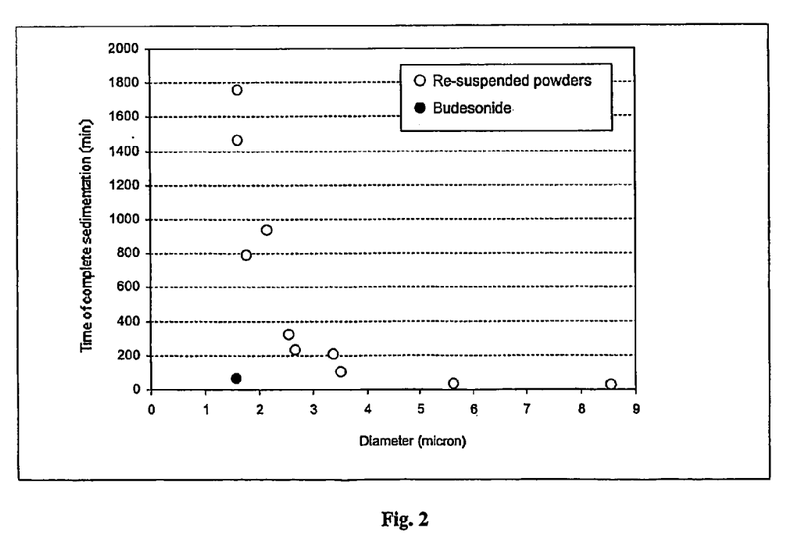
Figure 3:
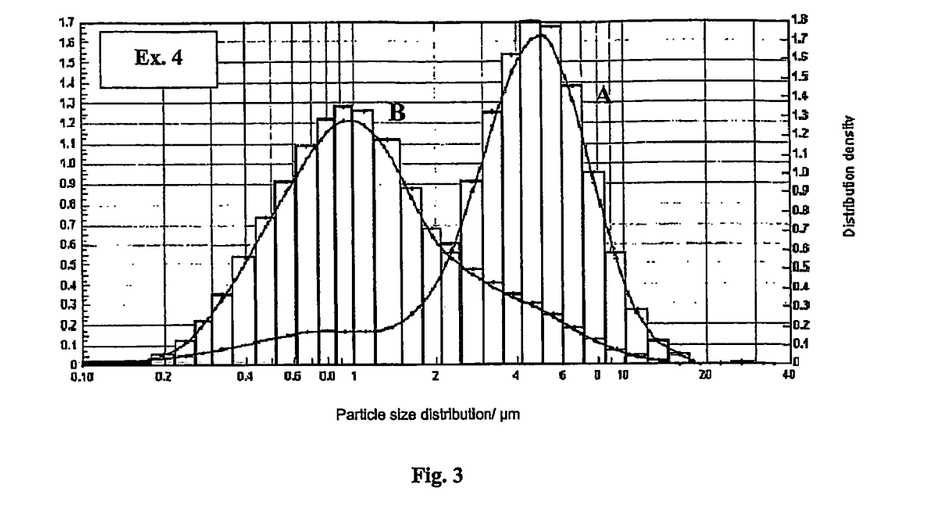
Figure 4:
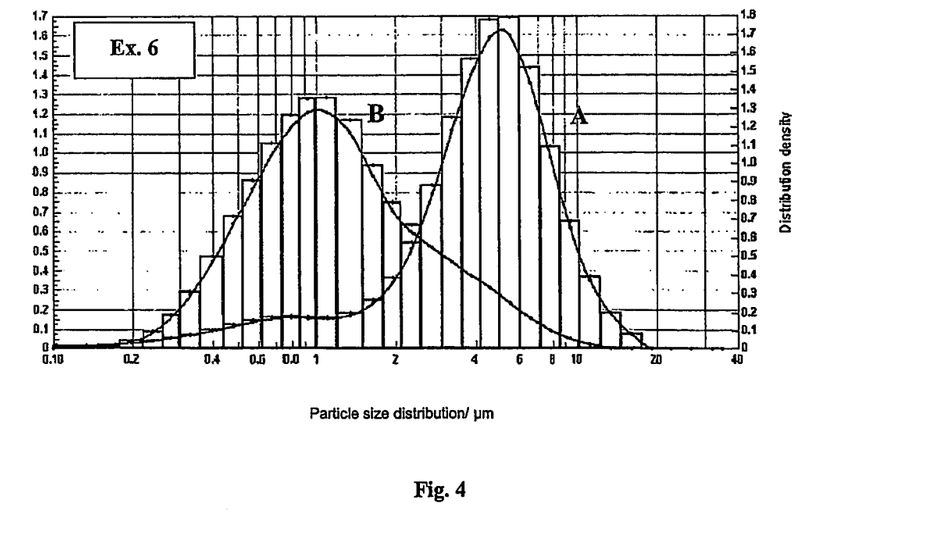
Figure 5:
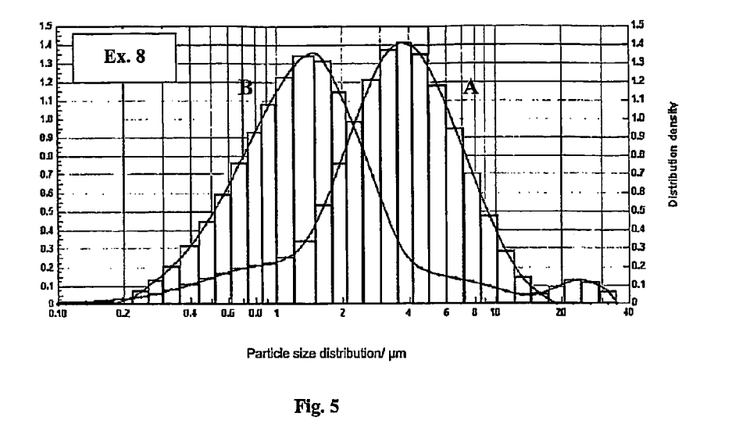
Figure 6:
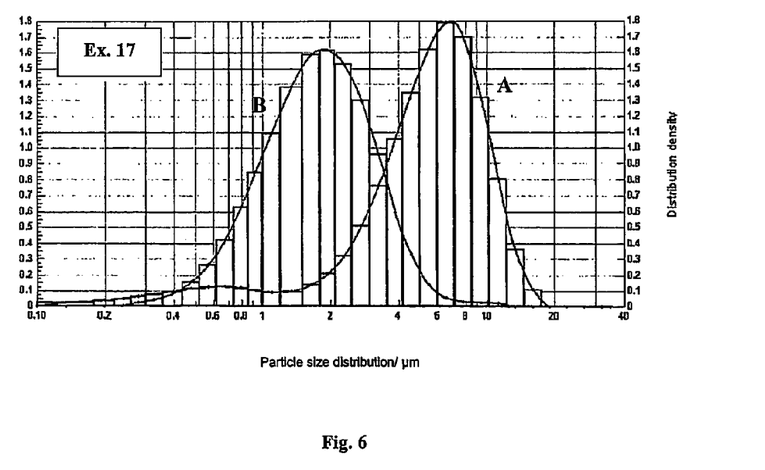

In order to deeply investigate such occurrences, the diagram reported in FIG. 2 has been drawn, in which the particle size evaluated by light scattering in humid state conditions is plotted against time of complete sedimentation evaluated with the Lumifuge centrifuge.

The graph shows a direct relationship between the particle size and the evaluated sedimentation time. The trend is hyperbolic, with fine particles tending to high sedimentation times and coarse particles for which the sedimentation time tends to be zero. The graph also shows that a crystalline powder like budesonide with a 1.59 μm, although dispersed in substantially the same liquid medium and kept in dispersion by a surfactant, has a sedimentation time much lower than that of a suspension of the invention with particles of about the same size.

According to a preferential aspect of the invention, the size distribution of the solid particles in the suspension maintains the substantial mono-modality of the dry powder composition precursor of the suspension, therefore avoiding the undesired aggregation occurrences of the particles, typical of known commercial pharmaceutical suspensions.

Another aspect of the invention consists of a kit of products for the extemporaneous preparation of a stable aqueous suspension of a hydrophobic active principle, comprising:

a) an effective amount of a dry pharmaceutical composition comprising said hydrophobic active principle, at least one water soluble excipient and at least one surfactant, as previously described;
b) a predetermined volume of a dispersing liquid medium;
wherein said products are filled in physically separated containers, in order to be mixed extemporaneously to form a suspension in which the Volume Mean Diameter $VMD_w$ of the particles in suspension is lower than the Volume Mean Diameter $VMD_d$ of the particles of said dry powder composition.

Preferably, the dispersing medium is water or a physiological solution, and its contact with the dry powder composition allows to prepare a suspension of the active principle according to the invention ready to be administered.

The invention will now be illustrated referring to the following examples, given as an illustrative but not limitative basis.

EXAMPLES

Preparation of the Solid Dry Composition

A) Preparation Based on a Solution

Examples from 1 to 14 and Comparative Examples 1 to 6

The preparation of the composition was carried out by mixing an aqueous solution of excipients with an organic solution of the active principle and dissolving the surfactants in either one of the two phases, according to the surfactant preferential solubility. The two solutions were then mixed to form a final clear solution. Said final solution was dried by spray drying using a Labplant SD 06 spray dryer according to the operative conditions indicated in table 1.

TABLE 1

| Example | Aqueous solution Phase (B) | | Organic solution Phase (A) | | Operative conditions | |
|---|---|---|---|---|---|---|
| 1 | Lactose | 43.65 g | Budesonide | 0.45 g | Inlet temp. (° C.) | 120 |
| | Tween 80 | 0.9 g | Ethyl alcohol | 90 ml | Feed rate (ml/min) | 3.0 |
| | Distilled water | 210 ml | | | Nozzle (diameter) | 0.5 |
| 2 | Lactose | 95.5 g | Budesonide | 0.5 g | Inlet temp. (° C.) | 120 |
| | Tween 80 | 4 g | Ethyl alcohol | 300 ml | Feed rate (ml/min) | 3.0 |
| | Distilled water | 700 ml | | | Nozzle (diameter) | 1.0 |
| 3 | Lactose | 49.25 g | Budesonide | 0.25 g | Inlet temp. (° C.) | 120 |
| | Tween 80 | 0.5 g | Ethyl alcohol | 150 ml | Feed rate (ml/min) | 3.0 |
| | Distilled water | 350 ml | | | Nozzle (diameter) | 1.0 |
| 4 | Lactose | 38.75 g | Budesonide | 0.25 g | Inlet temp. (° C.) | 120 |
| | Saccharose | 10.0 g | Ethyl alcohol | 150 ml | Feed rate (ml/min) | 3.0 |
| | Tween 80 | 1.0 g | | | Nozzle (diameter) | 1.0 |
| | Distilled water | 350 ml | | | | |
| 5 | Lactose | 48.75 g | Budesonide | 0.25 g | Inlet temp. (° C.) | 120 |
| | Tween 80 | 1.0 g | Ethyl alcohol | 150 ml | Feed rate (ml/min) | 3.0 |
| | Distilled water | 350 ml | | | Nozzle (diameter) | 1.0 |
| 6 | Lactose | 32.5 g | Budesonide | 0.25 g | Inlet temp. (° C.) | 120 |
| | Saccharose | 16.25 g | Ethyl alcohol | 150 ml | Feed rate (ml/min) | 3.0 |
| | Tween 80 | 1.0 g | | | Nozzle (diameter) | 1.0 |
| | Distilled water | 350 ml | | | | |
| 7 | Lactose | 9.75 g | Beclomethasone dipropionate | 0.05 g | Inlet temp. (° C.) | 120 |
| | Tween 80 | 0.2 g | Ethyl alcohol | 700 ml | Feed rate (ml/min) | 5.0 |
| | Distilled water | 300 ml | | | Nozzle (diameter) | 1.0 |
| 8 | Lactose | 8.705 g | Beclomethasone dipropionate | 0.05 g | Inlet temp. (° C.) | 120 |
| | NaCl | 1.125 g | Ethyl alcohol | 700 ml | Feed rate (ml/min) | 5.0 |
| | Tween 20 | 0.1 g | | | Nozzle (diameter) | 1.0 |
| | Span 20 | 0.02 g | | | | |
| | Distilled water | 300 ml | | | | |
| 9 | Lactose | 22.375 g | Budesonide | 0.125 g | Inlet temp. (° C.) | 130 |
| | Pluronic F68 | 2.5 g | Ethyl Alcool | 250 ml | Feed rate (ml/min) | 3.0 |
| | Distilled water | 250 ml | | | Nozzle (diameter) | 0.5 |
| 10 | Lactose | 9.7 g | Ursodiol | 0.1 g | Inlet temp. (° C.) | 130 |
| | Tween 80 | 0.2 g | Ethyl alcool | 250 ml | Feed rate (ml/min) | 3.0 |
| | Distilled water | 250 ml | | | Nozzle (diameter) | 0.5 |
| 11 | Lactose | 14.1 g | Ketoprofen | 0.45 g | Inlet temp. (° C.) | 130 |
| | Tween 80 | 0.45 g | Ethyl alcool | 250 ml | Feed rate (ml/min) | 3.0 |
| | Distilled water | 250 ml | | | Nozzle (diameter) | 0.5 |
| 12 | Lactose | 9.3 g | Ketoprofen | 0.3 g | Inlet temp. (° C.) | 130 |
| | Pluronic F68 | 0.4 g | Ethyl alcool | 250 ml | Feed rate (ml/min) | 4.0 |
| | Distilled water | 250 ml | | | Nozzle (diameter) | 2.0 |
| 13 | Lactose | 9.4 g | Ursodiol | 0.2 g | Inlet temp. (° C.) | 130 |
| | Pluronic F68 | 0.4 g | Ethyl alcool | 250 ml | Feed rate (ml/min) | 3.0 |
| | Distilled water | 250 ml | | | Nozzle (diameter) | 2.0 |
| 14 | Lactose | 8.95 g | Beclomethasone dipropionate | 0.05 g | Inlet temp. (° C.) | 130 |
| | Tween 20 | 0.1 g | Lipoid E-PC3 | 0.9 g | Feed rate (ml/min) | 5.0 |
| | Distilled water | 300 ml | Ethyl alcool | 700 ml | Nozzle (diameter) | 1.0 |
| Comp. 1 | Lactose | 3.45 g | Budesonide | 0.375 g | Inlet temp. (° C.) | 140 |
| | Benzalkonium Chloride | 0.2 g | Ethyl alcohol | 5 ml | Feed rate (ml/min) | 5.0 |
| | NaCl | 3.45 g | | | Nozzle (diameter) | 1.0 |
| | Distilled water | 495 ml | | | | |
| Comp. 2 | Lactose | 22.5 g | Budesonide | 0.45 g | Inlet temp. (° C.) | 120 |
| | NaCl | 22.05 g | Ethyl alcohol | 90 ml | Feed rate (ml/min) | 3.0 |
| | Distilled water | 210 ml | | | Nozzle (diameter) | 0.5 |

TABLE 1-continued

| Example | Aqueous solution Phase (B) | | | Organic solution Phase (A) | | | Operative conditions | |
|---|---|---|---|---|---|---|---|---|
| Comp. 3 | Lactose | 24.75 | g | Budesonide | 0.25 | g | Inlet temp. (° C.) | 130 |
| | Distilled water | 350 | ml | Ethyl alcohol | 150 | ml | Feed rate (ml/min) | 3.0 |
| | | | | | | | Nozzle (diameter) | 0.5 |
| Comp. 4 | Lactose | 9.95 | g | Beclomethasone dipropionate | 0.05 | g | Inlet temp. (° C.) | 130 |
| | Distilled water | 300 | ml | Ethyl alcohol | 700 | ml | Feed rate (ml/min) | 5.0 |
| | | | | | | | nozzle (diameter) | 1.0 |
| Comp. 5 | Lactose | 9.9 | g | Ursodiol | 0.1 | g | Inlet temp. (° C.) | 130 |
| | Distilled water | 250 | ml | Ethyl alcohol | 250 | ml | Feed rate (ml/min) | 3.0 |
| | | | | | | | nozzle (diameter) | 0.5 |
| Comp. 6 | Lactose | 14.55 | g | Ketoprofen | 0.45 | g | Inlet temp. (° C.) | 130 |
| | Distilled water | 250 | ml | Ethyl alcool | 250 | ml | Feed rate (ml/min) | 3.0 |
| | | | | | | | Nozzle (diameter) | 0.5 |

B) Preparation Based on a Suspension

Examples from 15 to 17 and Reference Example 7

The suspension was been prepared by using a homogenizer and by dispersing the micronized active principle in an aqueous solution including surfactant and excipient according to the amounts indicated in Table 2 in order to form a homogeneous aqueous suspension.

The obtained suspension was dried using a Labplant SD 06 spray dryer according to the operative conditions indicated in Table 2 and by keeping the suspension under continuous stirring during the drying process.

TABLE 2

| Example | Aqueous suspension Phase (C) | | | Operative conditions | |
|---|---|---|---|---|---|
| 15 | Lactose | 20.0 | g | Inlet temp (° C.) | 120 |
| | Sodium Chloride | 4.25 | g | Feed rate (ml/min) | 3.0 |
| | Tween 80 | 0.1 | g | Nozzle (diameter mm) | 0.5 |
| | Budesonide | 0.25 | g | | |
| | Distilled water | 500 | ml | | |
| 16 | Lactose | 72.75 | g | Inlet temp (° C.) | 120 |
| | Tween 80 | 1.5 | g | Feed rate (ml/min) | 3.0 |
| | Budesonide | 0.75 | g | Nozzle (diameter mm) | 0.5 |
| | Distilled water | 500 | ml | | |
| 17 | Lactose | 37.5 | g | Inlet temp (° C.) | 120 |
| | Sodium Chloride | 35.25 | g | Feed rate (ml/min) | 3.0 |
| | Tween 80 | 1.5 | g | Nozzle (diameter mm) | 0.5 |
| | Budesonide | 0.75 | g | | |
| | Distilled water | 500 | ml | | |
| Comp. 7 | Sodium Chloride | 8.42 | g | Inlet temp (° C.) | 120 |
| | Sodium Citrate | 0.5 | g | Feed rate (ml/min) | 3.0 |
| | Citric acid | 0.28 | g | Nozzle (diameter mm) | 0.5 |
| | Sodium EDTA | 0.1 | g | | |
| | Tween 80 | 0.2 | g | | |
| | Budesonide | 0.5 | g | | |
| | Distilled water | 1000 | ml | | |

Dry State Particle Size Distribution

The obtained powder was characterized in terms of dry state size distribution using a Sympatec Oasis light scattering instrument equipped with a Rodos dry disperser working at a 3 bar dispersing pressure and appropriate measuring lens able to analyze over the dimensional range 0.10-35.0 µm or alternatively measuring lens for the dimensional range 0.5-175.0 µm.

Determination of the Wet State Particle Size Distribution of the Particles of the Extemporaneous Suspension For the wet state particle size distribution an amount of powder, variable in relation of the amount of active principle, was dispersed in 50 ml of distilled water, corresponding to the capacity of a light scattering Sympatec Oasis wet state analyzer dispersion cell Sucell SVA (Small Volume Adapter), under stirring for at least 3 minutes, such as to detect, through the light scattering analyzer, an optimal stable light obscuration. The analysis was conducted using a lens in the dimensional range 0.10-35.0 µm or alternatively a lens in the dimensional range 0.5-175.0 µm.

Characteristics of Dry Powder Compositions and of Suspensions Prepared Extemporaneously Table 3 shows some data referred to dry powders, extemporaneous suspensions obtained from them, and also some comparative example data. Data reported in the table have the following meaning:

The number of the example is that of tables 1 and 2, except for comparative examples 8 and 9;

The composition in comparative example 9 is the following: NaCl 84.2 g; Sodium citrate 5.0 g; citric acid 2.8 g; Sodium EDTA 1.0 g; surfactant "Tween 80" 2.0 g; Budesonide 5.0 g.

The column "Surfactant ratio/Active principle" indicates the weight-to-weight ratio of these two species of the composition;

$VMD_d$ is the diameter of the particles in the dry composition (powder);

$VMD_w$ is the diameter of the particles in the extemporaneous suspension;

$VMD_w/VMD_d$ is the diameters ratio in the wet state and dry state.

The time of complete clarification of the extemporaneous suspension is calculated using the transmittance variation line, as previously indicated.

TABLE 3

| Example | Surfactant/active principle ratio | Dry state $VMD_d$ | Humid state $VMD_w$ | $VMD_w/VMD_d$ | K | Time of complete sedimentation $T_{100}$ (min) @ 300 rpm |
|---|---|---|---|---|---|---|
| PREPARATIONS BASED ON SOLUTIONS | | | | | | |
| 1 | 2 | 5.3 | 3.52 | 0.66 | 0.1608 | 103.65 |
| 2 | 8 | 5.22 | 2.17 | 0.41 | 0.0178 | 936.3 |

TABLE 3-continued

| Example | Surfactant/active principle ratio | Dry state $VMD_d$ | Humid state $VMD_w$ | $VMD_w/VMD_d$ | K | Time of complete sedimentation $T_{100}$ (min) @ 300 rpm |
|---|---|---|---|---|---|---|
| 3 | 2 | 5.03 | 2.56 | 0.51 | 0.0522 | 319.28 |
| 4 | 4 | 4.60 | 1.63 | 0.35 | 0.0114 | 1461.99 |
| 5 | 4 | 5.13 | 1.78 | 0.35 | 0.0212 | 786.16 |
| 6 | 4 | 4.87 | 1.63 | 0.33 | 0.0095 | 1754.4 |
| 7 | 4 | 4.88 | 3.39 | 0.69 | 0.0803 | 207.55 |
| 8 | 2.4 | 4.11 | 2.53 | 0.61 | 0.0253 | 658.76 |
| 9 | 20 | 6.02 | 2.03 | 0.34 | 0.1009 | 165.18 |
| 10 | 2 | 3.36 | 2.32 | 0.69 | 0.0169 | 986.19 |
| 11 | 1 | 6.74 | 4.38 | 0.65 | 0.1588 | 104.95 |
| 12 | 1.33 | 17.17 | 11.05 | 0.64 | 0.2199 | 75.79 |
| 13 | 2 | 24.58 | 5.25 | 0.21 | 0.1368 | 121.83 |
| 14 | 20 | 3.67 | 3.60 | 0.98 | 0.0288 | 578.7 |
| PREPARATIONS BASED ON SUSPENSIONS | | | | | | |
| 15 | 0.4 | 4.51 | 2.32 | 0.51 | 0.2272 | 73.36 |
| 16 | 2 | 6.09 | 2.29 | 0.37 | 0.1798 | 92.69 |
| 17 | 2 | 5.99 | 2.01 | 0.33 | 0.2413 | 69.07 |
| Comp. 7 | 0.4 | 2.82 | 5.63 | 1.99 | 0.4188 | 39.79 |
| PREPARATIONS WITHOUT SURFACTANT OR WITH AN INSUFFICIENT AMOUNT OF SURFACTANT | | | | | | |
| Comp. 2 | — | 4.81 | 5.28 | 1.09 | 2.5144 | 6.63 |
| Comp. 1 | 0.53 | 3.70 | 8.55 | 2.31 | 0.6134 | 27.17 |
| Comp. 3 | — | 3.21 | 9.62 | 3.00 | 0.2719 | 61.00 |
| Comp. 4 | — | 3.18 | 22.75 | 3.75 | — | — |
| Comp. 5 | — | 4.01 | 7.70 | 1.92 | 0.2273 | 73.32 |
| Comp. 6 | — | 5.05 | 9.81 | 1.94 | — | — |
| SUSPENSIONS OF COMPARISON | | | | | | |
| Comp. 8 | — | 1.59 | — | — | 0.264 | 63.0 |
| Comp. 9 | 0.40 | — | 3.67 | NA | 2.094 | 7.96 |

Comparative example 1 relates to a composition with the same components and amounts of example B-44 of U.S. Pat. No. 6,001,336 to Inhale Therapeutic Systems. It appears from Table 3 that when a suspension is made from said composition, the $VMD_w$ is greater than the $VMD_d$, differently from the compositions of the invention.

Comparative examples 2 and 3 are examples of Budesonide compositions without surfactant.

Comparative example 4 is an example of a Beclomethasone dipropionate composition without surfactant.

Comparative example 5 is an example of a Ursodeoxycholic Acid (Ursodiol) composition without surfactant Comparative example 6 is an example of a Ketoprofen composition without surfactant Comparative example 7 is an example of a composition with surfactant and excipients but with a $VMD_w/VMD_d$ ratio>1.

Comparative example 8 is referred to a suspension of just the active principle budesonide.

Comparative example 9 is referred to a composition similar to the commercial suspension Pulmaxan.

As table 3 demonstrates, examples 1-17 according to the invention refer to compositions which generate very stable extemporaneous suspensions with times of complete sedimentation greater than 60 minutes. Comparative examples 1, 2, 3, 4, 5, 6, 7 and 9, instead, refer to less stable suspensions, that means with complete sedimentation times firmly less than their corresponding extemporaneous suspensions. A particular case is comparative example 8, related to budesonide alone, not prepared using the spray drying process of the invention but obtained just suspending the active ingredient budesonide in a crystalline state. This is a low particle size active principle ($VMD_d$=1.59), therefore liable to the previously described dry-state handling problems. Where said suspensions are prepared by extemporaneous re-suspending of powders obtained from solutions (examples C1 to C6) or suspensions (example C7), Table 3 shows that they do not fulfil the relation $VMD_w/VMD_d<1$.

Determination of the Theoretical Mean Diameter of the Particles of the Active Principle in an Extemporaneous Suspension Using the previously described Stokes Equation which governs the sedimentation of a spherical particle in a liquid medium, the Theoretical Mean Diameter of the particles in the extemporaneous suspensions of the examples 1-14 was evaluated, using as a reference a suspension of micronized particles of the relevant active principle suspended in a solution having the same final composition of the corresponding suspension according to the invention. The obtained results are shown in the following Table 4.

TABLE 4

| Example | $VMD_w$ (μm) | τ (min) | $VMD_{wref}$ (μm) | $τ_{ref}$ (min) | TMD | $TMD/VMD_w$ |
|---|---|---|---|---|---|---|
| 1 | 3.52 | 103.65 | 1.97 | 86.27 | 1.80 | 0.51 |
| 2 | 2.17 | 936.30 | 2.03 | 150.83 | 0.81 | 0.38 |
| 3 | 2.56 | 319.28 | 1.97 | 111.56 | 1.16 | 0.45 |
| 4 | 1.63 | 1461.99 | 2.16 | 50.67 | 0.40 | 0.25 |
| 5 | 1.78 | 786.16 | 2.34 | 118.29 | 0.91 | 0.51 |
| 6 | 1.63 | 1754.40 | 2.09 | 57.0 | 0.38 | 0.23 |
| 7 | 3.39 | 207.55 | 7.65 | 32.73 | 3.04 | 0.90 |
| 8 | 2.53 | 658.76 | 5.56 | 94.86 | 2.11 | 0.83 |
| 9 | 2.03 | 165.18 | 2.53 | 59.25 | 1.52 | 0.75 |
| 10 | 2.32 | 986.19 | NA* | NA* | — | — |
| 11 | 4.38 | 104.95 | 22.10 | NA** | — | — |
| 12 | 11.05 | 75.79 | 24.96 | NA** | — | — |
| 13 | 5.25 | 121.83 | NA* | NA* | — | — |

TABLE 4-continued

| Example | $VMD_w$ (μm) | τ (min) | $VMD_{wref}$ (μm) | $τ_{ref}$ (min) | TMD | $TMD/VMD_w$ |
|---|---|---|---|---|---|---|
| 14 | 3.60 | 578.7 | NA* | NA* | — | — |
| 16 | 2.29 | 92.69 | 1.97 | 86.27 | 1.90 | 0.82 |

*Drug particles could not be dispersed efficiently in the liquid medium making impossible to measure $VMD_{wref}$ and $τ_{ref}$ for these preparations.
**Drug particles were too large and sedimented so fast that it was impossible to measure $τ_{ref}$ Table 4 shows that all reported compositions, prepared by spray drying, surprisingly behave in suspension as particles with a lower diameter than the actually evaluated one and are consistent with the relation TMD<$VMD_w$ FIG. 1 shows the particles size and the particles size distribution of a commercial suspension of beclomethasone dipropionate, evaluated using an Oasis Sympatec Light Scattering instrument equipped with a wet-state Sucell dispersion cell, previously mentioned. Said suspension appears to be bi-modal, with an important peak around 21 μm. Therefore the majority of the suspended particles have a size, expressed as VMD, greater than 5 μm.

It is obvious that the actually administrable drug dose in said suspensions, for an inhalation therapy, is heavily reduced due to evident particle aggregation, and consequent sedimentation phenomena.

FIGS. 3, 4, 5 and 6 show the dry state (curve A) and wet state (curve B) particle size distribution related to examples 4, 6, 8 and 17, respectively. More in particular, in each figure curve A shows the size distribution of the dry powder composition whose diameter is $VMD_d$, and curve B shows the size distribution of the particles in suspension whose diameter is $VMD_w$. It is noticeable that particles in suspension are always very fine and size distributions are always substantially mono-modal, that means that the particle size is substantially distributed around one peak.

Therefore, suspensions according to the invention are stable, they do not lead to aggregation or sedimentation and may be used to administer degradable drugs throughout prolonged contact with water, due to their extemporaneous preparation. Moreover, making available and putting on the market a dry powder composition allows for a simplification of the sterilization process and minimizing its microbial contamination, without necessarily using preservatives, like it is instead necessary with non-extemporaneous suspensions, stored for a long time.

Determination of the Aerosol Properties of Extemporaneous Suspensions Delivered Out of a Nebulizer.

In order to evaluate the aerosol properties of extemporaneous suspensions prepared from the dry pharmaceutical compositions described, an Apparatus C—Multi Stage Liquid Impinger (MSLI) as described in the European Pharmacopoeia was used.

The Multi Stage Liquid Impinger consists of 4 impaction stages and an integral filter stage (stage 5). A standard induction port was utilized with a suitable mouthpiece adapter to provide airtight seal between the nebulizer and the induction port.

According to its directions for use, 20 ml of an appropriate solvent mixture were introduced in each of stages 1 to 4.

The outlet of the Multi Stage Liquid Impinger was connected to a suitable vacuum pump and the flow adjusted to 30±1.5 liters per minute in order to determine a lower cut-off aerodynamic diameter corresponding to 9.62 μm for stage 2, 4.38 μm for stage 3 and 2.40 μm for stage 4.

The mouthpiece adapter was placed in position at the end of the induction port so that the mouthpiece end of the nebulizer, when inserted lined up along the horizontal axis of the induction port and the nebulizer was positioned in the same orientation intended for use.

The nebulizer utilized was the Clenny (marketed by Medel, Italy) loaded with 2 ml of suspension to be tested.

The pump was then switched on for 10 sec. before activating the nebulizer, aerosolizing for 5 consecutive minutes its content inside the impinger.

At the end of the 5 minutes the nebulizer had been turned off and 5 sec. later the pump was switched off.

The Multi Stage Liquid Impinger had been dismantled, carefully collecting the amount of active principle into aliquots of solvent and subsequently analyzing for active content deposited in each stage, in the induction port, on the mouthpiece adapter and residual in the nebulizer.

The total mass of active principle collected was within the range of 75 to 125 percent of the nominal drug dosage introduced in the nebulizer.

The compositions tested were: commercial budesonide and beclomethasone dipropionate products, budesonide and beclomethasone dipropionate suspensions prepared by mixing micronized active principles in a dispersing medium equivalent to the one of the commercial products and tested in order to evaluated the aerosol performance of a freshly prepared suspension in comparison to a commercial product whose manufacturing date can only be estimated through expiration date.

The compositions according to Example 1 and Example 8 represented extemporaneous suspensions containing budesonide and beclomethasone dipropionate.

The test performed was used to calculate for each preparation the Fine Particle Fraction (or FPF %) corresponding to the percentage of active drug that was delivered inside the impinger whose aerodynamic diameter was below 5.0 μm, the Mass Median Aerodynamic Diameter (MMAD) which corresponds to the calculated aerodynamic diameter that divides the particles of an aerosol (a gaseous suspension of fine liquids or solid particles) in half, based on the weight of the particles. 50% by weight of the particles will be larger than the MMAD and 50% will be smaller than the MMAD and the Geometric Standard Deviation (GSD) of the distribution corresponding to a dimensionless number equal to the ratio between the MMAD and either 84% or 16% of the particle size distribution.

MMAD and GSD together describe the particle size distribution of an aerosol.

To perform the calculations for MMAD and GSD the cumulative fraction of active ingredient versus cut-off diameter were plotted on log probability paper and the plot was used to calculate MMAD and GSD. The results are reported in Table 5.

The data reported in Table 5 indicate a substantial improvement in FPF and MMAD for Budesonide and Beclomethasone corresponding to Examples 1 and 8.

TABLE 5

| Example | FPF (%) | MMAD (μm) | GSD |
|---|---|---|---|
| Commercial budesonide suspension (Pulmaxan) | 27.3 ± 5.5 | 7.25 ± 1.38 | 2.57 ± 0.17 |
| Budesonide suspension | 29.3 ± 0.3 | 7.16 ± 0.06 | 2.33 ± 0.05 |
| Example 1 | 52.4 ± 0.6 | 4.14 ± 0.05 | 2.73 ± 0.01 |
| Commercial BDP | | | |

TABLE 5-continued

| Example | FPF (%) | MMAD (μm) | GSD |
|---|---|---|---|
| suspension (Clenil A) | 29.1 ± 0.5 | 6.99 ± 0.04 | 2.13 ± 0.01 |
| BDP suspension | 35.4 ± 1.4 | 6.16 ± 0.19 | 2.22 ± 0.02 |
| Example 8 | 48.3 ± 2.0 | 4.75 ± 0.23 | 2.48 ± 0.04 |

The invention claimed is:

1. Water suspension of solid particles for oral administration comprising a hydrophobic active principle, obtainable by dispersing in an aqueous medium a dry powder pharmaceutical composition comprising particles comprising said hydrophobic active principle, one or more water soluble excipients and one or more surfactants, characterized in that the Volume Mean Diameter, $VMD_w$, of the particles in said suspension determined under standard conditions of dispersion is lower than the Volume Mean Diameter, $VMD_d$, of the particles in said dry powder composition, the size distribution of the particles in dry powder form and in the suspension is monomodal, and that said surfactant and said active principle have a weight-to-weight ratio from 0.6 to 40 in said dry powder composition.

2. The water suspension according to claim 1, wherein the complete sedimentation time of said suspension is greater than 40 minutes.

3. The water suspension according to claim 2, wherein the complete sedimentation time of said suspension is greater than 60 minutes.

4. The water suspension according to claim 3, wherein the complete sedimentation time of said suspension is greater than 100 minutes.

5. The water suspension according to claim 1, wherein the theoretical mean diameter TMD of said particles is lower than the Volume Mean Diameter, $VMD_w$.

6. The water suspension according to claim 5, wherein the theoretical mean diameter, TMD, of said particles fulfils the equation $TMD \leq 0.5\, VMD_w$.

7. The water suspension according to claim 1, wherein said active principle is a steroid molecule.

8. The water suspension according to claim 7, wherein said active principle is a glucocorticosteroid.

9. The water suspension according to claim 8, wherein said glucocorticosteroid is selected from the group consisting of budesonide, beclomethasone, fluticasone propionate, and mixtures thereof.

10. Kit of products for an extemporaneous preparation of a liquid suspension of a hydrophobic active principle, characterized by comprising:
a) an effective amount of a dry powder pharmaceutical composition comprising particles comprising said hydrophobic active principle, at least one water-soluble excipient and at least one surfactant, in which said surfactant and said active principle have a weight-to-weight ratio from 0.6 to 40,
b) a predetermined volume of an aqueous dispersing medium; wherein said products a) and b) are packaged in physically separated containers, in order to be mixed extemporaneously to form a suspension, in which the particles' Volume Mean Diameter, $VMD_w$, measured in standard conditions of dispersion is lower than the Volume Mean Diameter, $VMD_d$, of the particles in said dry powder pharmaceutical composition, and the size distribution of the particles in dry powder form and in the suspension is monomodal.

11. The kit of products according to claim 10, wherein the Volume Mean Diameter $VMD_d$ of the particles in said dry powder composition is from 0.1 to 175 μm.

12. The kit of products according to claim 11, wherein the Volume Mean Diameter $VMD_d$ of the particles in said solid dry composition is from 0.5 to 30 μm.

13. The kit of products according to claim 12, wherein the Volume Mean Diameter $VMD_d$ of the particles in said solid dry composition is from 1 to 10 μm.

* * * * *